Figure 1:
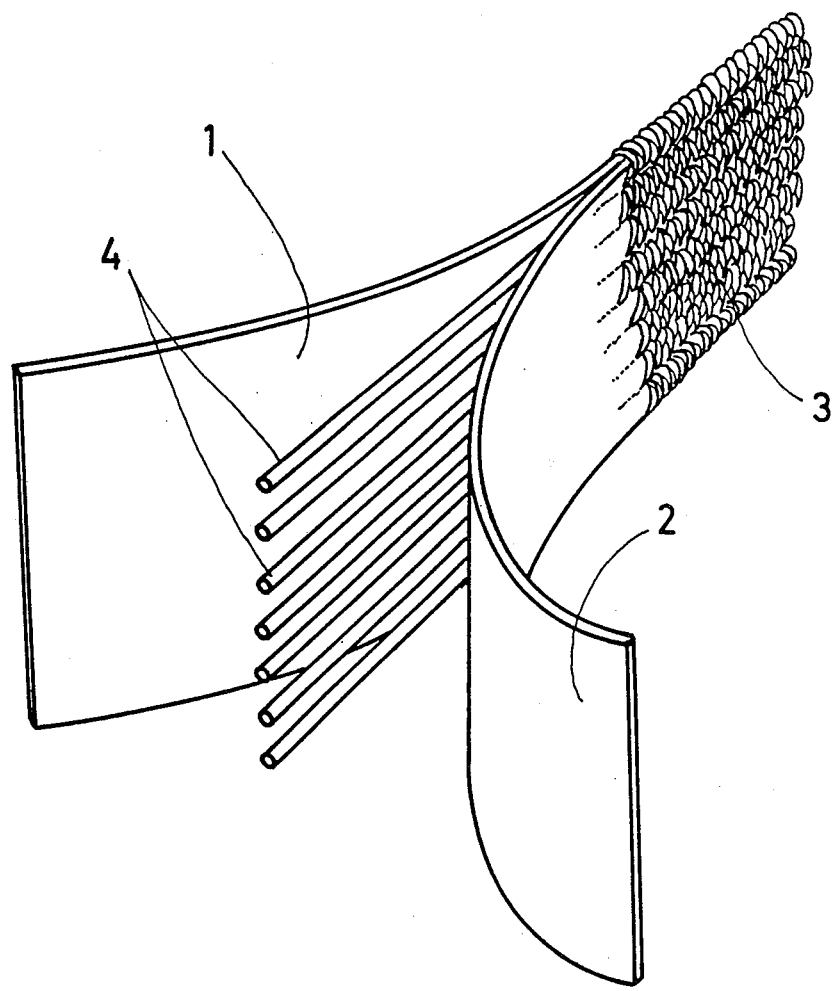

United States Patent [19]

Aichele

[11] Patent Number: 4,756,942

[45] Date of Patent: Jul. 12, 1988

[54] ELASTIC FABRIC

[75] Inventor: Dieter A. Aichele, Riehen, Switzerland

[73] Assignee: Vitapharm Basel AG, Basel, Switzerland

[21] Appl. No.: 96,402

[22] Filed: Sep. 15, 1987

[30] Foreign Application Priority Data

Sep. 18, 1986 [CH] Switzerland ............. 3742/86

[51] Int. Cl.⁴ .................................. B32B 3/06
[52] U.S. Cl. ............................ 428/102; 428/114;
428/192; 428/284; 428/292; 428/294; 428/231;
428/913
[58] Field of Search ............. 428/102, 114, 192, 294,
428/292, 294, 231, 913

[56] References Cited

U.S. PATENT DOCUMENTS

| 2,069,413 | 2/1937 | Leadbetter | 428/102 |
| 3,868,729 | 3/1975 | Lynam | 428/102 |
| 3,895,151 | 7/1975 | Matthews et al. | 428/102 |
| 4,043,062 | 8/1977 | Lehrman | 428/102 |
| 4,445,951 | 5/1984 | Lind et al. | 428/102 |
| 4,518,640 | 5/1985 | Wilkens | 428/102 |

Primary Examiner—James J. Bell
Attorney, Agent, or Firm—Wenderoth, Lind & Ponack

[57] ABSTRACT

An elastic fabric which can be used for bandages or dressings, formed with two strips of fabric which comprise, between them, a row of elastic threads in the longitudinal direction, the elastic threads being subjected to a tension greater than that of the strips of fabric and the whole being joined together by a series of stitches forming a weft, so that the surface of the fabrics at rest is shirred, is described.

4 Claims, 2 Drawing Sheets

ELASTIC FABRIC

The present invention refers to improvements in the manufacture of elastic fabrics which can be used especially for bandages and dressings.

Elastic fabrics intended for direct application onto the skin must have a surface with non-irritating properties. Likewise, clothes manufactured with these fabrics must be free from seams, hems, welts and the like, which produce unevenness when pressure is applied and on their surface. It is also important that the materials employed for the manufacture of such clothes are well tolerated by the human body, are resistant to washing, are totally harmless and can be moulded to the shape of the body.

At present, attempts are being made to achieve the objectives mentioned above by surface-polishing of the elastic fabric, which results solely in a decrease in its thickness. In order to compensate for the disadvantages of a thin fabric, it is usually finished, but this only adds another disadvantage to the fabric, given that the finishing agent makes the fabric water-proof and that it is a chemical additive; additionally, the effect is only short-lived.

In addition to all this, seams and joints always prove to be difficult to achieve in a very fine fabric; additionally, if fine gauge elastic threads are employed, they must be woven while being highly stretched in order to obtain the same pressure, which restricts the possible elasticity percentage and the characteristic life of the fabric.

Considering the points mentioned above and in order to overcome the disadvantages and problems presented by currently available fabrics intended for bandages and clinical articles, the improvements which form the subject of the present invention were invented, with a view to producing a fabric having a surface which is pleasant to touch, which can be combined with self-adhesive closures, whose manufacture does not require hems at edges or at welts, which allows sweat to pass through it and which has a sideways elasticity.

A fabric with these properties is well suited for the manufacture of elastic strips, one or both ends of which may be supplied with adhesive-type closures, which facilitates its application because loosening or possible slipping are thereby prevented.

From the fabric which forms the subject of the invention, it is possible to manufacture articles such as gauntlets or ankle supports, which adapt to the shape of the body and which find applications in thermotherapy and pressure therapy. These articles, reinforced with tapes of adhesive material and covered with a strip for additional safety, provide adaptable bandages for a variable degree of immobilization or correction.

It is possible, therefore, to manufacture, in particular, girdles for post-operative use, corsets for post-operative use after fat removal (cosmetic surgery); brassieres for post-operative use in cosmetic surgery; compression bandages for burns, amputations and angiological applications (oedemas, varicose veins, and the like); elastic sweatbands for sportsmen, wristbands, headbands and the like, trusses for newborn babies and other articles which require direct contact of the fabric with the skin.

In general, the improved elastic fabrics according to the invention comprise a piece of fabric, an elastic warping, another piece of the same or a different fabric, the whole being joined together by a chain-stitch or elastic stitch which joins the two pieces of fabric and at the same time covers the elastic threads. This process is carried out with the elastic threads under tension, which tension is much greater than the tension that the two or three fabrics employed actually have or could have.

The result is an elastic fabric obtained by sewing two more or less elastic or totally rigid fabrics with elastic overstitches, which have a core, an elastic filling which constrains it, shrinks it and shirrs it, the two rough surfaces being maintained at rest, still being flexible, it being possible for one of them to be made of polyamide which makes it suitable for attaching an adhesive-type closure.

Therefore, a fabric, one or both surfaces of which are suitable for receiving an adhesive closure and which are very pleasant to the skin, is obtained. The surface in contact with the skin may be made of polyamide, but it may also be made of looped or curled cotton; it is also possible to apply a fabric on one of the surfaces, inserting or placing thread in its position, producing a brushed finish of a suitable thread, acrylic, woollen and the like, on the surface. The result is a brushed surface, more or less hairy like a blanket; the other surface may be provided with an adhesive-type closure made of cotton, absorbent cotton-wool or any other textile material such as wool or any mixture which can be obtained.

In order to make it easier to understand the invention, a plate with drawings in which one embodiment is shown, by way of example, is attached to the present specification.

In the drawings

FIG. 1 gives a perspective view of the components of the bandage.

Figure 2:
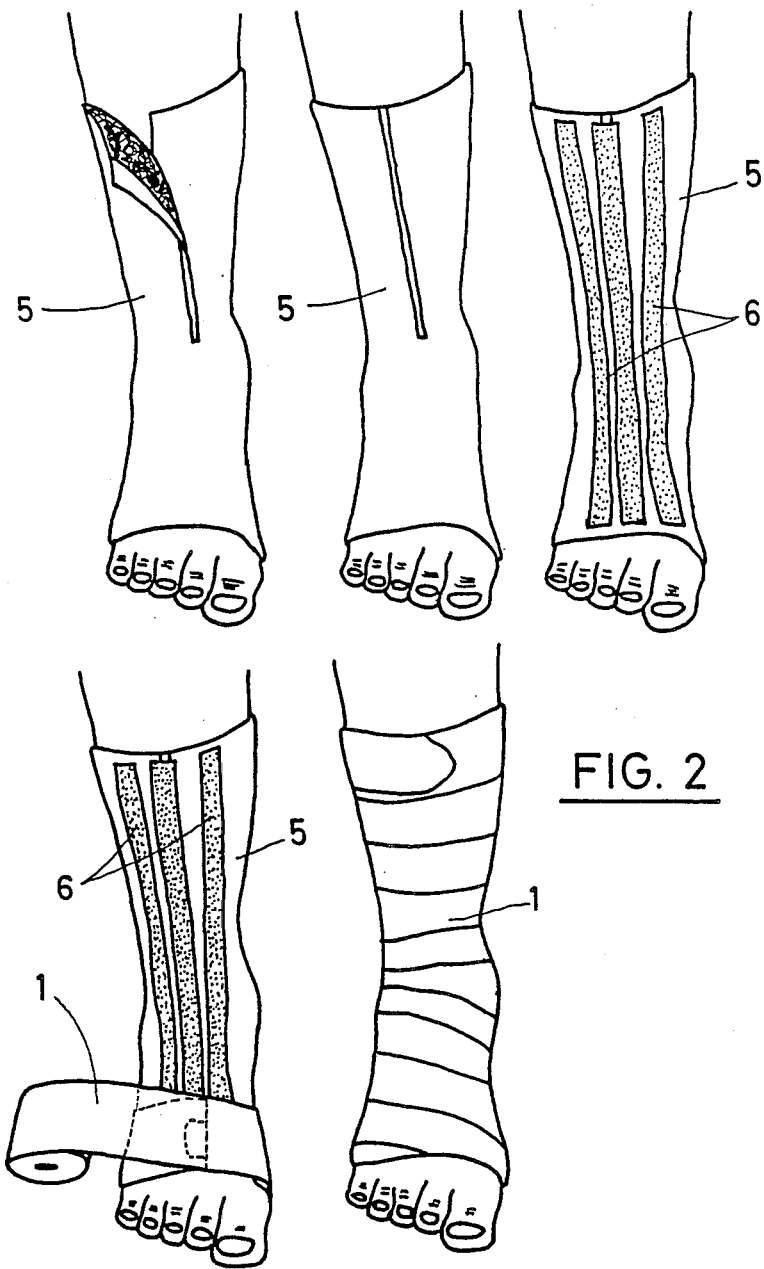

FIG. 2 illustrates the use of the bandage, in combination with an ankle support, so as to obtain an adaptable bandage for a variable degree of immobilization or correction.

Referring to the figures, there can be seen the view of an elastic bandage which comprises a first piece of fabric 1, a second piece 2 of the same or a different fabric, the whole being joined together by a "chain-stitch" or elastic stitch 3, which joins the two pieces of fabric 1 and 2 and at the same time covers the elastic threads 4, which have a tension greater than the tension the two or three fabrics employed actually have or could have.

One or both surfaces of the fabric may be suitable to be provided with a self-adhesive closure. Likewise, the components of the bandage may both be made of polyamide, acrylic and polyamide, or cotton and polyamide.

FIG. 2 illustrates a practical example of use of the bandage in combination with an ankle support 5, to which self-adhesive tapes 6 have been attached, which are covered with a strip of the type described, which gives adaptable bandages for a variable degree of immobilization.

In essence, the invention may be put into practice in the form of other embodiments which differ in detail from that given above by way of example and which also fall within the scope of the invention. It may be produced in all shapes and sizes with the most appropriate materials, all of which remain within the spirit of the claims.

I claim:

1. Improved elastic fabric, which can be used, in particular, for bandages and dressings, characterized in that it comprises a first strip of fabric and a second strip of fabric made of the same or a different fabric, both being made of a material which is pleasant to touch, permeable to sweat and having a sideways elasticity, the two strips of fabric being placed against each other in the lengthwise direction and comprise, between them, a row of elastic threads positioned parallel to each other in the longitudinal direction and subjected to a tension which is greater than that of the fabric strips, and the whole is joined together by a series of stitches forming a weft, going from one edge to the other in the transverse direction and passing on either side of the elastic threads from the outer face of one to the outer face of the other fabric so that the surface of the fabric at rest is shirred.

2. Elastic fabric according to claim 1, characterized in that one or both of the fabric strips are made of polyamide or of looped cotton.

3. Elastic fabric according to claim 2, characterized in that one of the fabric strips is made of polyamide and comprises, at one of its ends, a self-adhesive type closure.

4. Elastic fabric according to claim 1, characterized in that it additionally comprises, on one of the outer surfaces, a third strip of the same or a different fabric joined to the whole by a series of stitches forming a weft as described in claim 1.

* * * * *